US 8,877,129 B2

(12) United States Patent
Brandenburg

(10) Patent No.: US 8,877,129 B2
(45) Date of Patent: Nov. 4, 2014

(54) METHOD AND DEVICE FOR OPTICAL DETECTION OF SUBSTANCES IN A LIQUID OR GASEOUS MEDIUM

(75) Inventor: Albrecht Brandenburg, Freiburg (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 1091 days.

(21) Appl. No.: 12/174,294

(22) Filed: Jul. 16, 2008

(65) Prior Publication Data
US 2009/0069199 A1  Mar. 12, 2009

(30) Foreign Application Priority Data

Jul. 16, 2007  (DE) .................. 10 2007 033 124

(51) Int. Cl.
G01N 21/64 (2006.01)
G01N 21/00 (2006.01)
G01N 33/552 (2006.01)
G01N 33/554 (2006.01)
G01N 33/543 (2006.01)
G01N 33/544 (2006.01)
G01N 21/77 (2006.01)

(52) U.S. Cl.
CPC .......... G01N 21/6452 (2013.01); G01N 33/552 (2013.01); G01N 21/648 (2013.01); G01N 33/54366 (2013.01); G01N 33/544 (2013.01); G01N 21/7703 (2013.01)
USPC ..................................... 422/82.11

(58) Field of Classification Search
CPC ............ G01N 21/6452; G01N 21/648; G01N 21/7703; G01N 21/64; G01N 21/00; G01N 33/552; G01N 33/54366; G01N 33/544; G01N 33/00

USPC ...................................... 422/82.11
See application file for complete search history.

(56) References Cited

U.S. PATENT DOCUMENTS

| 3,308,709 | A |   | 3/1967  | Harrick           |
|-----------|---|---|---------|-------------------|
| 3,436,159 | A |   | 4/1969  | Harrick et al.    |
| 3,486,829 | A |   | 12/1969 | Wilks, Jr.        |
| 3,556,659 | A |   | 1/1971  | Hawes             |
| 4,775,637 | A |   | 10/1988 | Sutherland et al. |
| 4,815,843 | A | * | 3/1989  | Tiefenthaler et al. ......... 356/128 |
| 5,037,199 | A |   | 8/1991  | Hlousek           |
| 5,239,360 | A |   | 8/1993  | Moring et al.     |

(Continued)

FOREIGN PATENT DOCUMENTS

| DE | 19611025 A1 | 9/1997 |
| DE | 19732619 A1 | 2/1999 |

(Continued)

Primary Examiner — Christine T Mui
(74) Attorney, Agent, or Firm — Rader, Fishman & Grauer PLLC

(57) ABSTRACT

The invention relates to a device for optical detection of substances in a liquid or gaseous medium, with a substrate with molecules for detecting the substances that are to be detected, wherein these molecules are immobilized at a surface of the substrate or in the substrate and wherein the substances that are to be detected can essentially be selectively bound to these molecules, wherein light waves can be coupled into the substrate and can be guided through this, and wherein the substrate is a foil element made of a transparent material in which a coupling structure for coupling the light waves is integrally formed and in which the coupled light waves can be guided.

29 Claims, 6 Drawing Sheets

(56) References Cited

U.S. PATENT DOCUMENTS

| | | |
|---|---|---|
| 5,344,784 A | 9/1994 | Attridge |
| 5,362,445 A | 11/1994 | Miyahara et al. |
| 5,372,783 A | 12/1994 | Lackie |
| 5,565,365 A | 10/1996 | Glass |
| 6,120,734 A | 9/2000 | Lackie |
| 6,198,869 B1 | 3/2001 | Kraus et al. |
| 6,211,954 B1 | 4/2001 | Danielzik et al. |
| 6,239,871 B1 | 5/2001 | Gilby |
| 6,462,809 B1 | 10/2002 | Ryan et al. |
| 6,469,785 B1 | 10/2002 | Duveneck et al. |
| 6,498,353 B2 | 12/2002 | Nagle et al. |
| 6,707,561 B1 * | 3/2004 | Budach et al. ............ 356/521 |
| 6,939,576 B2 * | 9/2005 | Deshpande et al. ........ 427/223 |
| 6,951,715 B2 * | 10/2005 | Cunningham et al. ........ 435/4 |
| 6,979,567 B2 * | 12/2005 | Herron et al. ............ 435/287.1 |
| 2001/0055797 A1 * | 12/2001 | Conroy et al. ............ 435/177 |
| 2002/0034457 A1 * | 3/2002 | Reichert et al. ........... 422/82.11 |
| 2003/0133640 A1 | 7/2003 | Tiefenthaler |
| 2004/0091862 A1 * | 5/2004 | Brandenburg et al. ........ 435/6 |
| 2005/0110898 A1 | 5/2005 | Ryu |

FOREIGN PATENT DOCUMENTS

| | | |
|---|---|---|
| DE | 10036457 A1 | 2/2002 |
| DE | 10052165 A1 | 5/2002 |
| DE | 10227962 A1 | 1/2004 |
| DE | 10251893 A1 | 5/2004 |
| DE | 102005038256 A1 | 3/2006 |
| DE | 102007021544 A1 | 11/2008 |
| EP | 0184600 A1 | 6/1986 |
| EP | 0519622 A2 | 12/1992 |
| EP | 0620429 A1 | 10/1994 |
| EP | 1085315 A1 | 3/2001 |
| EP | 1347284 A1 | 9/2003 |
| WO | WO-8607149 A1 | 12/1986 |
| WO | WO-9205426 A1 | 4/1992 |
| WO | WO-9427137 A2 | 11/1994 |
| WO | WO-9626432 A1 | 8/1996 |
| WO | WO-9635940 A1 | 11/1996 |
| WO | WO-9822803 A1 | 5/1998 |
| WO | WO-0235214 A1 | 5/2002 |
| WO | WO-2005003743 A2 | 1/2005 |
| WO | WO-2005047939 A1 | 5/2005 |

* cited by examiner

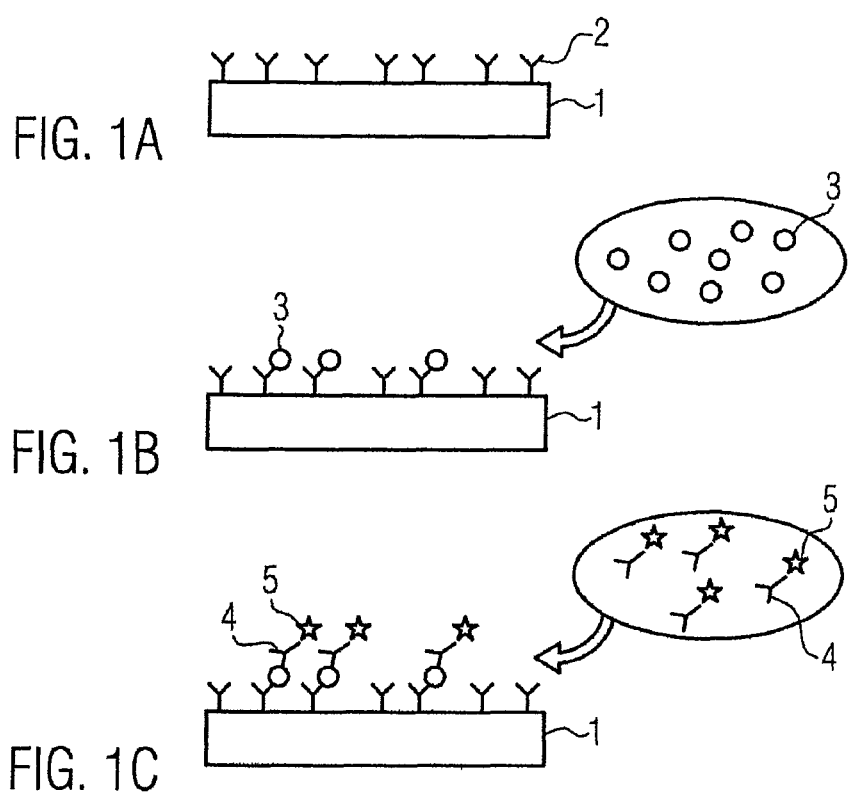

METHOD AND DEVICE FOR OPTICAL DETECTION OF SUBSTANCES IN A LIQUID OR GASEOUS MEDIUM

CROSS REFERENCE TO RELATED APPLICATIONS

This application is a National Phase Application related to DE 102007033124.1 which was filed on Jul. 16, 2007 which application is incorporated herein by reference in its entirety.

TECHNICAL FIELD

The present invention relates to a device for the optical detection of substances in a liquid or gas-phase medium according to independent claim 1, particularly a biochip and/or a microarray. In addition, the present invention relates to a method for the production of a substrate for molecules for the purpose of recognizing said substances, for use in this device. In addition, the present invention also relates to a method and device for spatially resolved detection of chemical reactions on a surface (of the substrate).

Chemical reactions occurring close to a surface are particularly used as indicators of analytes in liquid samples. For this purpose, so-called probe molecules are immobilized—that is, chemically bonded—to the surface of a substrate. Probes are molecules which bond to the analyte being investigated. This bonding should occur in a substantially selective manner, such that a bonding event is exclusively an indication of the presence of the analyte being investigated (the substance being searched for).

By producing numerous probes on the (measuring-) surface of the substrate in the form of measuring points of a so-called microarray, it is possible for numerous indicative reactions to proceed in parallel on a small surface, wherein at different points on the surface, different types of compounds are bonded as probes.

In many cases, it is advantageous to carry out the analysis in the presence of the sample. If there is only a small volume of the sample available for this purpose, then microfluid components can be used on the surface to bring the sample into contact with the surface.

The analytes which will adsorb onto the surface can be DNA molecules, preferably DNA single strands, for example. In this case, DNA molecules are also bonded to the surface as probes, for example. These analyte molecules (that is, the substances being investigated) can bond to said probes by means of a so-called hybridization reaction if the sequences of the nucleotide bases are complementary to each other. Moreover, it is possible to selectively detect certain DNA sequences at one point of the microarray.

A further possibility exists in the immobilization of antibodies as probes on the surface, the same specifically binding the respective antigen.

A method for reading out a measuring array (=for detection of the analyte(s)) should be able to identify very small amounts of the analyte (the substance being investigated) upon bonding of the same to the probes. The detection should also be able to occur in a space-resolved manner in this case, such that it is possible to analyze multiple substances in parallel.

The use of such (identification-) methods occurs in the field of medical diagnostics, for example. In this case, bodily fluids are used as analytic samples, such as whole blood, serum, plasma, saliva, or urine. In some cases, pre-treatment of the sample is necessary. In addition, it is also necessary for reliably diagnosing certain illnesses to analyze multiple parameters in parallel.

Other areas of application are the analysis of foods and water, e.g. with respect to pathogenic germs, as well as forensics.

In general, electrical, electrochemical, and optical detection principles can be used for indicating the bonding of the analyte molecule (that is, the substance being investigated) to the probes immobilized on the surface. In addition, there are also gravimetric and calorimetric methods.

SUMMARY

One of the electrical methods involves the generation of strong electric fields on the surface by means of microelectronic arrays with very small contact pitch. A redox reaction takes place on the surface by means of the action of other reagents, and generates an electrical signal.

The optical methods are nearly entirely optical fluorescence detection methods. Optical fluorescence detection requires a fluorescing molecule, because the analyte molecules being investigated generally do not fluoresce on their own.

The fluorescent dyes are then detected by a suitable optical system.

This marking can be achieved in that the analyte itself is marked with the dye before the bonding reaction to the surface takes place.

As an alternative to this approach, it is also possible to attach a further substance which is marked with a fluorescent dye to the surface after the analyte has bonded successfully to the respective probe, wherein said substance in turn only bonds to analyte molecules which are already bonded. So-called sandwich assays proceed in this manner using two antibodies (one bonded antibody and another antibody which is marked and attaches later.

In addition, there exists the possibility of carrying out a so-called competitive test, wherein a marked substance is used which bonds to the probe in competition with the analyte.

BRIEF DESCRIPTION OF THE DRAWINGS

The invention at hand is described in more detail below based on preferred exemplary embodiments combined with associated drawings. In the figures,
FIG. 1A to FIG. 1C show the creation of a sandwich assay.

DETAILED DESCRIPTION

Figure 2A:
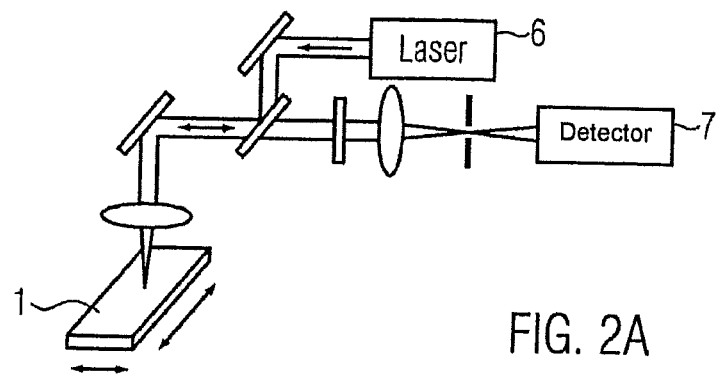
FIG. 2A to FIG. 2D show known detection methods for reading out the fluorescence biochip.

This basic approach used in optical fluorescence detection by means of a sandwich assay is schematically illustrated in FIG. 1A to FIG. 1C. In FIG. 1A the surface 1 is illustrated with antibodies 2. As illustrated in FIG. 1B, the corresponding antigens 3 (the substance being investigated) adsorb onto these antibodies 2. The addition of a second antibody 4 is illustrated in FIG. 1C. This second antibody 4 is marked with a fluorescent dye 5. The second, marked antibody adsorbs at this point onto the substance being investigated (the antigen) 3.

Methods for reading out fluorescent microarrays (biochips) optically are schematically illustrated in FIG. 2. As far as is known, such biochips are always washed after the reaction with the sample, dried, and finally read out in an optical system which recognizes the fluorescent markers in a space-resolved manner. In this case, an image of the chip is produced which portrays the distribution of the intensity of fluorescence on the surface of the biochip. These images are frequently further evaluated with methods for image processing. In this case, the intensity of fluorescence integrated via one measuring point is typically evaluated following removal of the background (background radiation).

Figure 2B:
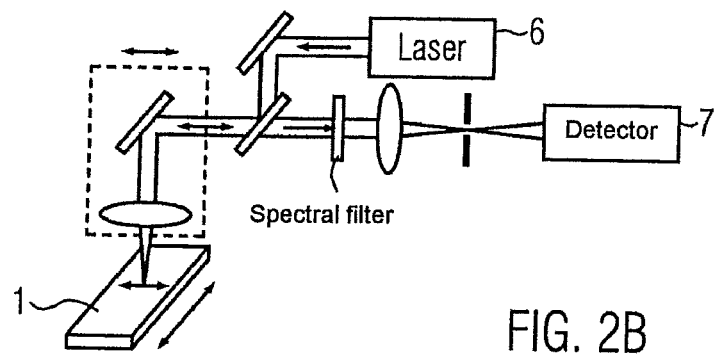
Figure 2C:
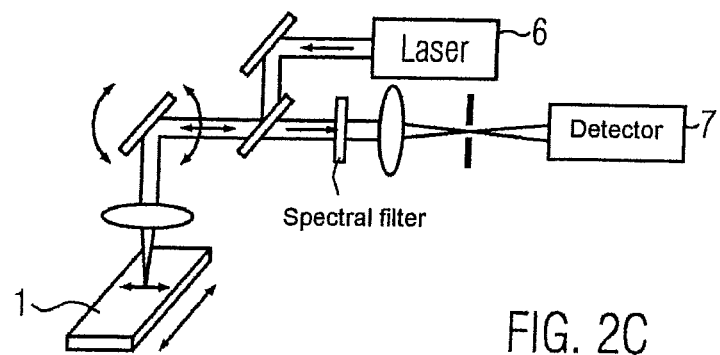

Laser scanners are primarily used for detecting the intensity of fluorescence, wherein a focus of a laser 6 is moved over the surface 1. By means of this laser focus, the fluorescent marker is excited in a localized manner. The fluorescence light is typically sensed by a photomultiplier 7 as the detector. The scanning process proceeds in a corresponding manner, either by rapid movement of the biochip in two spatial dimensions (a "moving stage"), as is schematically illustrated in FIG. 2A, or by the rapid movement of part of the optics in the path of the excitation light ("flying optics"), as is schematically illustrated in FIG. 2B, or by a rotating scanner mirror which is positioned in the path of the excitation light in front of the focusing lens ("pre-objective scan"), as is schematically illustrated in FIG. 2C.

Figure 2D:
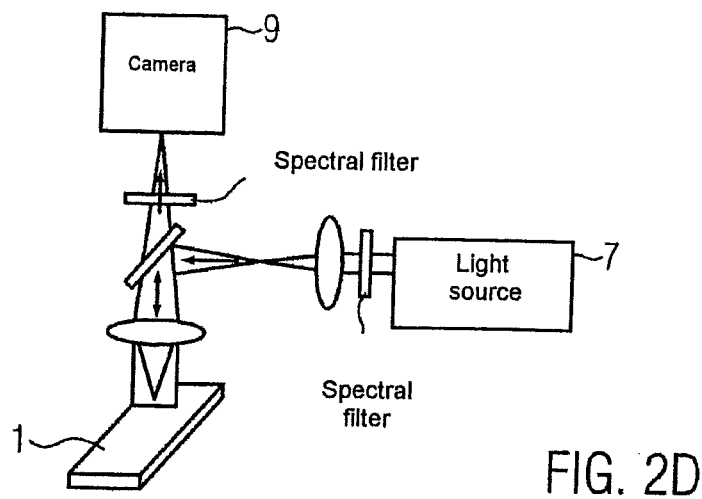

In addition to laser scanners, imaging systems are also used, wherein the surface of the biochip, or a part thereof, is illuminated, as is schematically illustrated in FIG. 2D. In this case, the radiation generated by a light source 8 is projected onto the surface 1 of the substrate, and the resulting fluorescence light is sensed by a camera, particularly by a CCD camera.

In the detection method described in FIG. 2A to FIG. 2D, the upper or lower side of the biochip is always illuminated. However, if it is desired to take measurements when the sample is still present, then the fluorescent marker molecules (fluorochromes) which are not bonded and are in the solution above the biochip will also be excited to fluorescence. As such, the background radiation increases and significantly increases the detection threshold of the measuring system, and thereby worsens the measurement precision.

Figure 3:
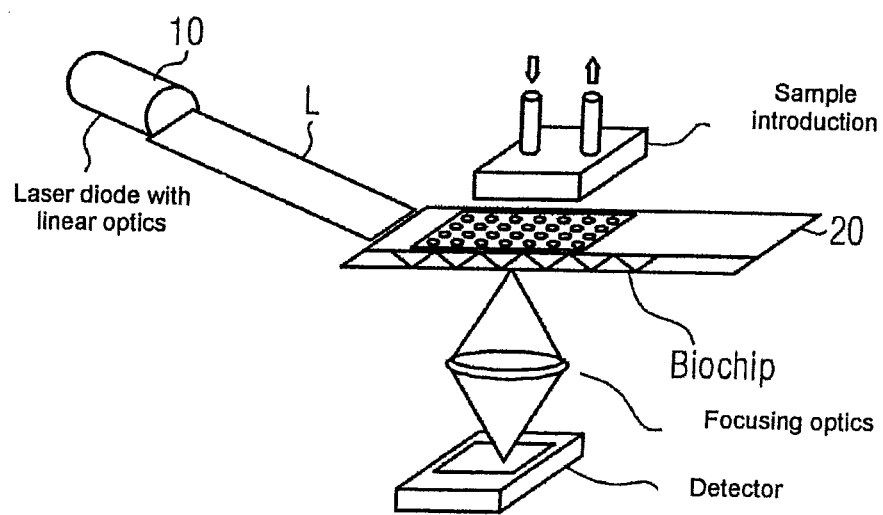
FIG. 3 shows a TIRF arrangement with a planar glass medium.

One possibility of circumventing this problem would exist in using TIRF technology (total internal reflection fluorescence), which is illustrated in FIG. 3. In this arrangement, laser light L is generated by means of a laser diode 10 with linear lenses, input coupled into the biochip 20, and guided along the biochip 20. The excitation of fluorescent light occurs via the evanescence field of the input coupled laser beam light, and exclusively within a very small distance from the biochip surface (approx. 50-300 nm, depending on the optical arrangement).

The biochip required for use of TIRF technology can be realized by preparing standard object slides in such a manner that it is possible to input couple light through one edge of the glass of the object slide. This prepared edge must be polished for this purpose, such that the light can be input coupled into the biochip without being scattered. Such object slides which are suitable for a corresponding preparation are typically approx. 1 mm thick, such that the laser can be very efficiently input coupled into the polished edge.

However, it would be advantageous if the thickness of the substrate were substantially smaller. In this case, the efficiency of the fluorescence excitation would be particularly significantly higher. The efficiency of the fluorescence excitation can in this case be estimated by calculating the number of reflections on the surface of the biochip per unit of length. With a decreasing chip thickness and the same beam angle relative to the chip surface, the number of reflections increases; however, the light intensity of light passing through the biochip is significantly reduced after a short distance. The beam angle, in contrast, is determined by the total internal reflection critical angle at which total reflection transitions to partial transmission. If the coupling angle with respect to the normal on the surface is significantly higher than this critical angle, then the evanescence field is significantly reduced at the surface. This results in worsening of the efficiency of the fluorescence excitation.

The then significantly more difficult coupling of light into the prepared edge however makes it impossible to use significantly thinner glass slides for the biochip. At glass thicknesses below 500 µm, the polishing and the overall manual manipulation of the biochip become significantly more difficult.

For the purpose of avoiding this disadvantage, it could be attempted to shape the end surfaces in such a manner that an acceptable input coupling efficiency is achieved even in combination with minimal thickness of the glass slide. As such, lens-shaped structures, by way of example, could be formed, by means of which the light is focused into the glass slide. However, such structures are difficult to manufacture.

A further disadvantage of the "front-side" input coupling of light into the glass slide results from the fact that the seal between the sample container placed on the glass slide, or a flow-through cell, disturbs the guiding of light at this cell, and generates additional losses.

Figure 4:
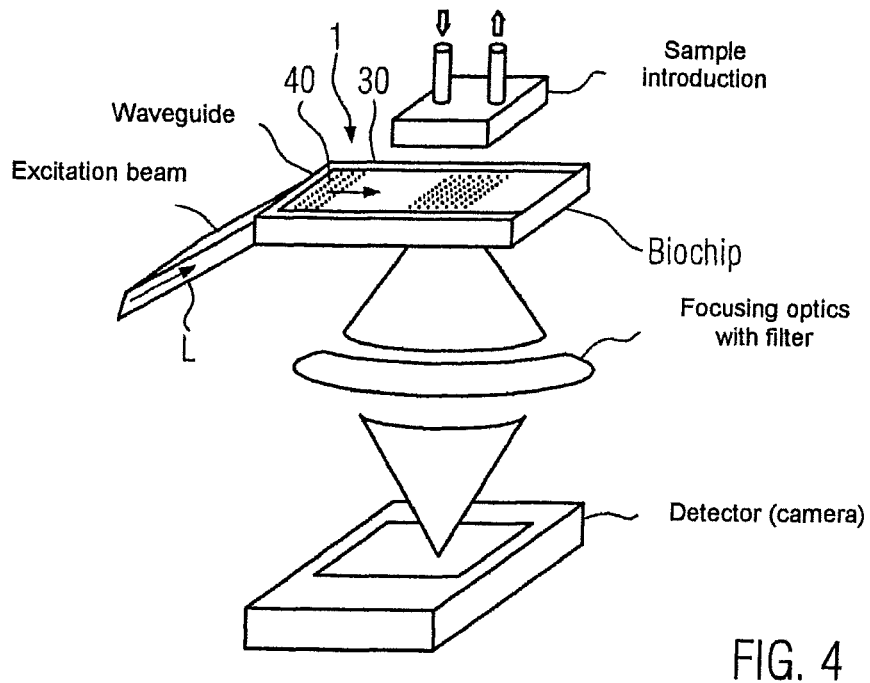
FIG. 4 shows a thin-film waveguide with grid coupling.

The prior art suggests further reducing the thickness of the waveguide by applying a waveguide as a thin coating on a substrate, as is illustrated in FIG. 4, which shows a thin-film waveguide with grating coupling. In this case, the light beam L is once again input coupled into the waveguide 30 via the diffraction grating 40 at the "front-side" of the waveguide.

By means of such a solution, it has been possible to realize waveguide thicknesses below approx. 150 nm, which significantly increases the intensity of the evanescence field. However, in this case, the input coupling of the light is more difficult. As a rule, diffraction gratings which are etched into the surface of the glass slide are used to achieve the input coupling of light. This process step is a very expensive procedure, due to the minimal structure size of the grating (period length of approx. 300 to 400 nm), and requires a clean room setup. In addition, in the case of these diffraction gratings, a significant scattering of the light guided in the waveguide has been observed even with very minimal surface roughness on the surface of the waveguide (several nm). As such, if the fluorescent light is not filtered perfectly, the background of the recorded image is significantly elevated. Because the noise of the background image substantially determines the detection threshold, the actual advantage of the higher evanescence field fraction can no longer be fully exploited.

One problem addressed by the present invention is that of avoiding the disadvantages of the TIRF method discussed above, particularly with respect to reading out biochips—that is, the complex process steps accruing in the manufacture of biochips which are necessary in order to input couple light into the waveguide (edge polishing or structuring of diffraction gratings), because these two steps increase the cost of producing the biochip to such a degree that the biochip is not competitive on the market.

The problem described above is addressed according to the invention by a device for the optical detection of substance in a liquid or gas-phase medium, having a substrate with molecules for the purpose of recognizing the substances being investigated, said molecules being immobilized on a surface of the substrate or in the substrate, wherein the substances being investigated can bond to said molecules in a substantially selective manner, and light waves can be input coupled into the substrate and can be guided through the same, and the substrate is a film element made of a transparent material, wherein an input coupling structure for the purpose of input coupling light waves is integrally included in the same, and the input coupled light can be guided in the same.

In this case, the input coupling structure can be formed on the surface of the film element in one step together with the formation of the film element, during the shaping process for the film element itself.

In addition, the film element can be produced by means of stamping, rolling, casting, or curing from a liquid medium.

In addition, the input coupling structure can already be present in the mold used for said stamping, rolling, or injection molding, such that it is possible to produce the input coupling structure in one step at the same time as the production of the film element, and particularly the surface thereof, using this mold.

The present device can also have a flow cell for the medium being investigated, wherein said flow cell forms a measuring chamber together with the surface of the film element, and the input coupling structure is arranged in the area covered by the flow cell.

The molecules for the purpose of recognizing the substances being investigated can be probes comprising of biological and/or biochemical molecules, selected from the group consisting of antibody molecules, DNA molecules, DNA single strands, RNA molecules, RNA single strands, and mixtures thereof; the same being immobilized on the surface of the film element or in the film element.

The present device can also have a plurality of (such) molecules for the purpose of recognizing the substances being investigated, said molecules being immobilized on the surface of the film element or in the film element, and forming a read-out field (microarray) having a plurality of measuring points for the purpose of detecting the substances being investigated in a space-resolved manner.

The film element can also have a homogenizing area which is arranged in the beam path downstream from the input coupling structure and upstream from a measuring point, particularly in front of the read-out field, such that the light waves input coupled into the film element via the input coupling structure have a homogeneous distribution prior to reaching the measuring point.

In addition, an element which homogenizes the light waves, particularly a diffractive optical element such as a grating structure, can be provided in the beam path downstream from the input coupling structure and upstream from a measuring point.

In addition, the coupling structure can have a curve which is comparable to a cylindrical lens, or have a round shape, in order to achieve a homogeneous distribution of the light sources input coupled into the film element via the input coupling structure.

The input coupling structure can also be a refractive optical element such as a prism or a grating or a structure having a trapezoidal or rectangular cross-section.

The input coupling structure can likewise be a diffractive optical element.

A thickness of the film element can lie in the range between 10 μm and 1000 μm.

A thickness of the film element can be selected in such a manner that the film element possesses flexibility, and the film thickness is particularly approx. 100 μm.

The film element can be molded during the shaping process with a thicker area, particularly in the form of a frame, the same increasing the mechanical stability of the film element.

The device can also have a polymer cartridge into which the film element is integrated, and which has an injection port for the medium being investigated, a reagent container, liquid channels for transporting the medium and the reagents, and devices for moving the medium and reagents.

In addition, the device can have excitation optics for generating the light waves, particularly for exciting a marker used for the purpose of optical detection, such as a fluorescent dye, or for generating a color change on the surface or in the film element according to the medium being investigated.

In addition, the device can have a device for changing a relative position of the excitation optics to the input coupling structure, wherein an input coupling angle can be selected by means of said device in such a manner that the input coupling angle approximately corresponds to the total internal reflection critical angle, the latter arising from the refractive index of the medium bounding on the film element.

In addition, the device can have an output coupling structure for the purpose of output coupling the light waves, wherein said structure is formed on the surface of the film element in one step together with the formation of the film element itself during the shaping step for the film element.

The output coupling structure can be a refractive optical element such as a prism or a grating, or a structure having a trapezoidal or rectangular cross-section, or a diffractive optical element.

A detector can be arranged in the beam path downstream from this output coupling structure, and light waves output coupled from the output coupling structure can be detected by means of said detector—particularly for the purpose of optimizing the beam position and/or determining the scattered light of the input coupled light waves.

The detector can be provided for the purpose of detecting an intensity of the light waves at the output coupling structure to determine an absorption of the light waves guided in the film element, and the change thereof.

The device can also be made of an optically transparent plastic made of organic polymers, such as poly(methyl methacrylate), polystyrene, polycarbonate, PEG, and polyolefins, or of copolymers such as COC.

In addition, the film element can be made of a glass which is produced by hot embossing.

With respect to process technology, the problem addressed by the invention is solved by a method for the production of a substrate for molecules for recognizing substances in a gas-phase or liquid medium, for use in the present device, wherein the substances being investigated can bond to the probes in a substantially selective manner, and wherein the substrate is produced with a particular shape by means of stamping, rolling, casting, or curing from a liquid medium in such a manner that both the surface and an input coupling structure for the purpose of input coupling light waves are formed in one production step.

Plastic films can be used as the starting material for the substrate, wherein said plastic films are processed using a mold tool at high temperature. In this case, particularly metal elements processed by micromilling, or silicon wafers with structures applied by means of anisotropic etching, or rolls can be used as the molds.

The substrate can likewise be produced by means of molding, particularly injection molding.

As an alternative, the substrate can be produced from a liquid medium by means of curing of the medium in a mold. The curing process can be triggered by UV radiation in the case of special media suited to this purpose (UV-curable plastics).

Figure 5:
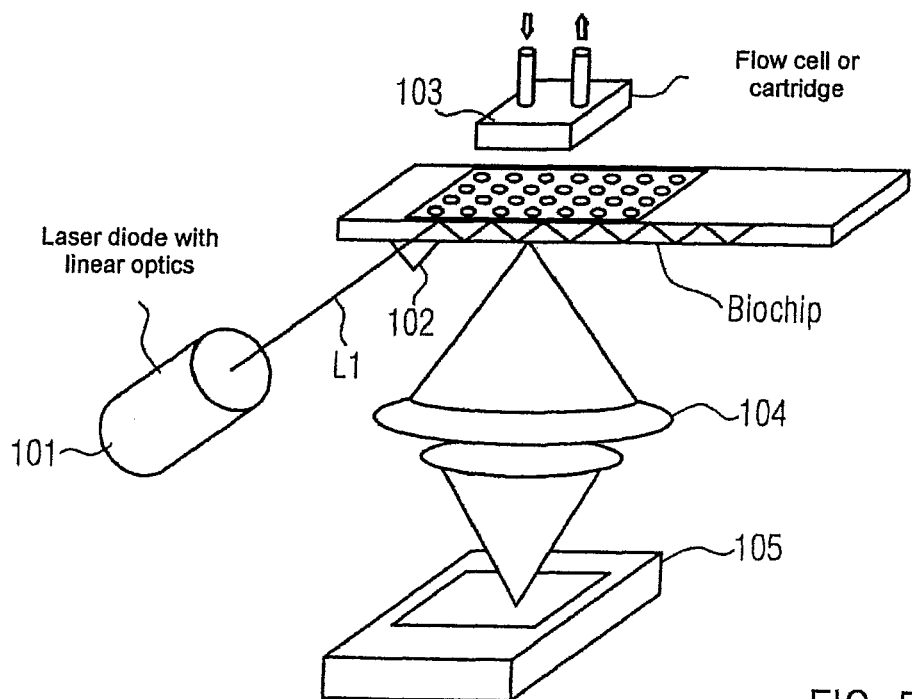
FIG. 5 shows a foil sensor according to one exemplary embodiment with a carrier element with coupling structure.

FIG. 5 shows a foil sensor as biochip (microarray) made of a thin polymer foil, wherein the excitation light is carried in the polymer foil 100. The excitation light L1 is generated via a laser diode with linear optics 101. The excitation light L1 is coupled via an optical structure 102, hereinafter referred to as coupling structure. This coupling structure 102 is integrated into the foil surface together with the machining process of the foil itself.

The machining process can e.g. be an embossing process. An embossing process is capable of achieving extremely smooth surfaces without expensive additional steps, where light is reflected without any relevant diffusion, and therefore the light transmission in the polymer foil is virtually lossless and creates a low amount of background irradiation.

Furthermore, a rolling process or a molding process, in particular an injection molding process can be used. It is also conceivable to produce the polymer foil from a liquid medium by hardening it.

As a common feature of all these different manufacturing processes, the coupling structure is in any case manufactured during the machining step of the foil element itself at the surface of the foil element together with the creation of the surface of the foil element.

During the embossing or (injection) molding process, the structure for coupling the light is defined by the shape used for the embossing and injection molding process. This process can be performed very cost-efficiently for large quantities and therefore, the biochip costs are extremely low.

In the exemplary embodiment at hand, the coupling structure 102 is not created in the marginal area (i.e. at the edges) of the foil 100. In fact, the coupling structure 102 is created in an area of the foil 100 which is covered by a flow cell 103, only illustrated schematically in FIG. 5 and not taking into consideration the actual size ratios. This achieves that the seal of the flow cell 103, e.g. the specimen container does not impair the light transmission in the foil element 100. In addition, the manufacture of the thin foils is significantly easier if the marginal area of the carrier (i.e. the end of the foil structure) does not require a special shape, so that the foil elements 100 with the previously molded-in coupling structure 102 can easily be punched out of the material after the machining process.

The coupling structure 102 can for instance be created as a prism structure, as implied schematically in FIG. 5. Alternatively, other shapes can also be used, such as e.g. square cross-sections or round shapes.

Rounded shapes, similar to a cylindrical lens, for example cause the light to focus into the foil. It is essential that the coupling structure comprises one or a plurality of surfaces whose orientation deviates from the one of the foil surface.

Figure 7A:
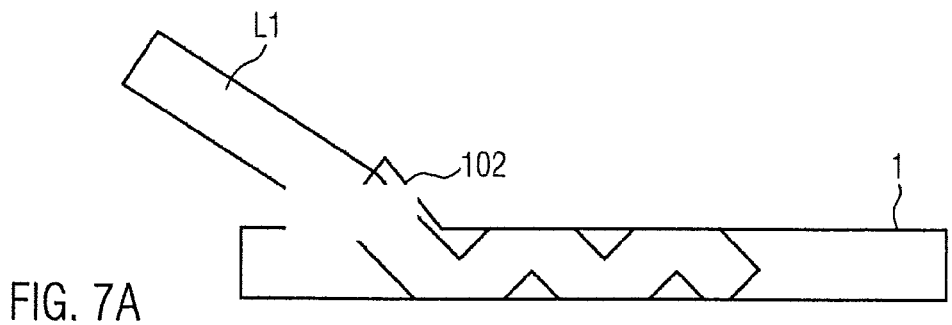
FIG. 7A to FIG. 7D show other exemplary embodiments of the carrier element with different coupling structures.
Figure 7B:
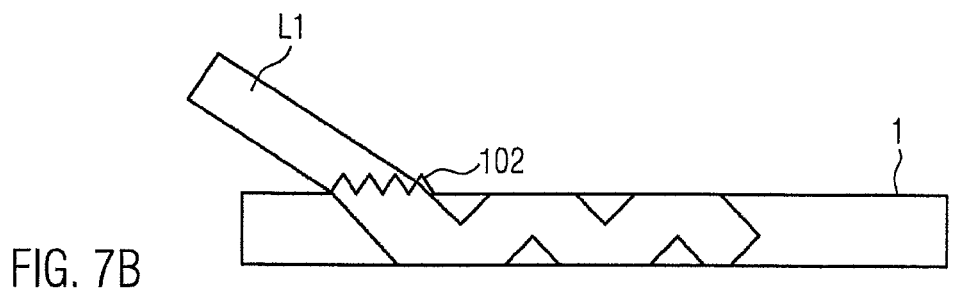
Figure 7C:
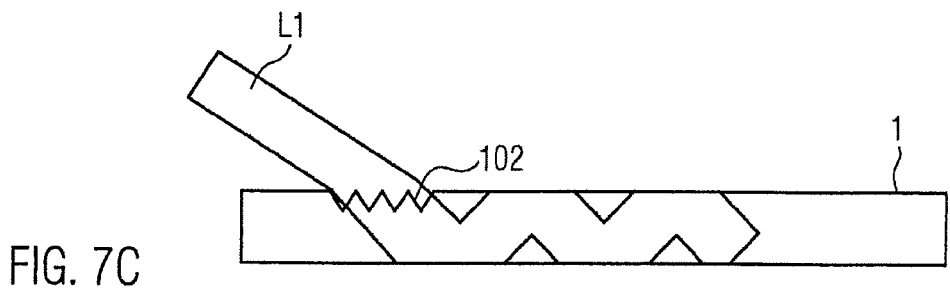

Furthermore, a plurality of structures can be combined as illustrated in FIG. 7B. This arrangement allows the coupling or a defined beam cross-section in the presence of a significantly lower structural height than in the presence of a single, larger structure (cp. FIG. 7A). Moreover, the coupling structures can also have the form of a recess, as illustrated in FIG. 7C. If the dimensions of these structures are significantly greater than the wavelength of the light, the diversion of the beam into the foil is essentially achieved by the refraction of the light on the surface of the structures.

Figure 7D:
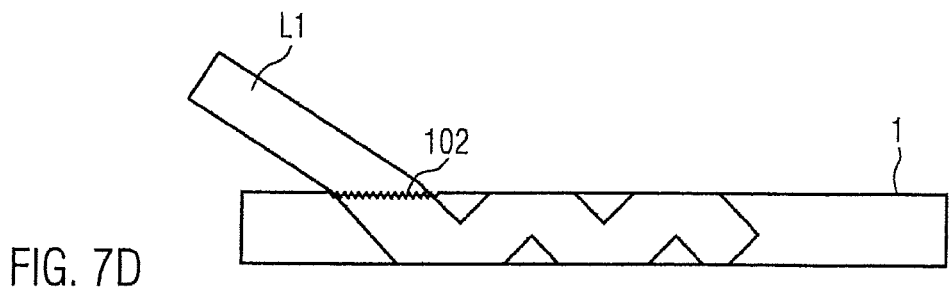

Grid structures are another option, because it is possible to transmit very fine structures in good quality to the polymer surface with the mentioned manufacturing methods. In this case, the structures of the coupling element are so small that the deflection of the light is essentially achieved with the diffraction of the light, cp. FIG. 7D.

Figure 6A:
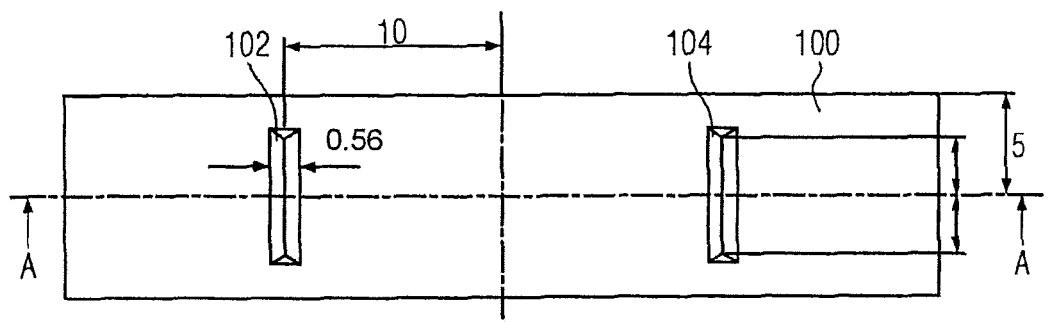
FIG. 6 shows a foil with prism-shaped coupling and decoupling structures used to create the foil sensor at hand.
Figure 6B:
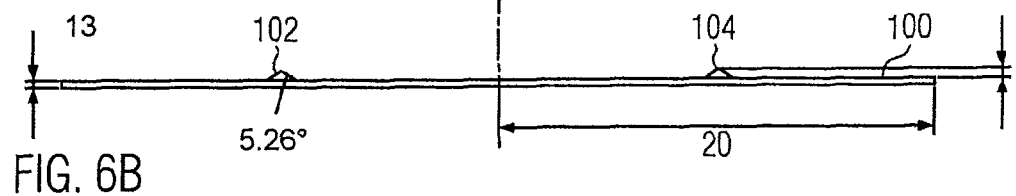

FIG. 6 illustrates a usable foil with a coupling structure 102 and a decoupling structure 104 (which is described in detail below), wherein the coupling structure 102 and the decoupling structure 104 are prism-shaped coupling structures. In the process, FIG. 6 shows both a top view in FIG. 6a as well as a cross-section along section A-A. Furthermore, exemplary dimensions in mm can be gathered from FIG. 6 used to describe a realized exemplary embodiment of the foil sensor.

Typically, the foil thickness ranges from 10 µm to 1,000 µm (130 µm in the exemplary embodiment at hand). Analogously, the foil sensor possesses a certain degree of flexibility, making it possible to adjust the foil sensor to different geometric shapes.

For very thin foils, an outer thicker area, such as in the form of a frame, will be provided in the molding process, providing greater mechanical stability to the foil sensor which is helpful for handling the foils.

Foils as illustrated can be integrated into a polymer cartridge which comprises additional functions. Said polymer cartridges can comprise in particular an injection port for the sample to be analyzed, reagent flasks, fluidizing chambers to transport the media (sample, reagents) and appliances to move the media in the cartridge.

Furthermore, complete solutions, e.g. for on-site diagnostics (POCT: point of care testing) can be realized with a polymer cartridge with already integrated foil sensor, which are very easy to handle and can be produced as disposable items.

The excitation optics 101 can be realized with a plurality of different light sources. Laser sources, LEDs, gas discharge tubes or other light sources can be used. However, lasers are preferably used for their good irradiation quality. For cost reasons, semi-conductor lasers are preferable, provided the emission wavelength is suitable for exciting the respective used indicator (colorant).

The light beam is collimated and dilated if necessary after the creation.

Next, a line is created with a cylindrical lens which is aimed at the coupling prism (102).

In the process, the corresponding coupling angle is selected in such a way that it closely corresponds to the total reflective angle resulting from the index of refraction of the adjacent medium.

Because the foils and cartridges are usually not placed into the corresponding appliance with the required positional accuracy, the exemplary embodiment at hand provides for an automatic movement of the beam in one direction perpendicular to the line created with the cylindrical lens. The position is changed in such a way with said automated positioning device that a maximum coupling efficiency is achieved.

The beam position is ultimately optimized by means of a measurement, either at a second coupling site (i.e. the decoupling structure 104) or by determining the diffused light of the light transmission.

The homogeneity of the excitation is a key parameter to ensure the comparability of the measurement at different locations on the chip. In the perpendicular direction with respect to the beam dissemination, the homogeneity is usually ensured with the corresponding selection of divergence and beam formation optics. However, in the direction of the beam, a modulation of the light intensity is determined immediately after the coupling. Because of the focus on the coupling prism 102, a very homogeneous distribution is achieved at a certain distance from the coupling prism (usually 5 to 10 mm, depending on the actual foil sensor image formations). Accordingly, at least one homogenization area subsequent to the coupling optics 102 is planned.

As explained above, the light coupling can also be automatic, usually by re-adjusting the position of the beam onto the prism. For this purpose, a detector is arranged behind the decoupling lens (the decoupling prism 104), used to detect the light decoupled from said prism. Optimizing this intensity also optimizes the intensity of the light carried in the foil.

The detection of the substances to be detected is performed by means of an imaging lens 104 which is ideally combined with a spectral light filter. The excitation light can be removed from the detector beam path by means of said filter. In addition, it is possible to reduce the background which is created amongst other things by the fluorescence inherent to the foils.

A variety of local resolution detectors can be used for the detection. A camera 105 is used according to the exemplary embodiment illustrated in FIG. 5. The sensitivity of this detection appliance 105 is an important aspect, because it is necessary that very low concentrations of fluorescent markers (fluorochromes) on the surface are still detected. CCD cameras used without or with the cooling of the CCD chip are suitable for this purpose. Cooling the CCD chip reduces the dark current in connection with high integration times, thus allowing the registration of low light intensities.

The entire device is controlled with a PC or a different microcontroller. The images are also collected and processed essentially automatically by means of the PC or microcontroller.

In addition to the detection of the fluorescence light, the carried light can be decoupled again via decoupling structure 104, wherein other measuring functions can be realized.

Possible materials for the foils include optically transparent plastics, such as e.g. polymethyl methacrylate, polystyrene, polycarbonate, PEG and polyolefin. Moreover, co-polymers are also possible, such as e.g. COC. Aside from organic polymers, glasses are also possible which can be hot foil stamped.

As explained above, the foils with the integrated coupling structures 102, 104 can be manufactured with different shaping methods for plastics.

The starting material for embossing foils are foils which are processed with a die at high temperatures. Forms used for this purpose can be e.g. metal elements processed with micro-mill. Alternatively, silicon wavers can be used, in which structures are integrated by means of anisotropic etching, using e.g. KOH. The advantage of this type of manufacture of the foil sensors is that the surface roughness is extremely low. However, when using silicon wafers, the usable angle of the created surfaces is restricted to certain values specified by the respective crystal structure of the silicon and the used crystal cut. If the structure depths are low (e.g. when using coupled grids), photolithographically structured surfaces with subsequent isotropic etching are also advantageous.

Other possible methods to manufacture the polymer structure of the foil element include rolling and embossing with UV hardening of the polymer. Moreover, injection molding can be used.

The description at hand discloses an optical system, in particular for the detection of fluorescent molecules on a surface of a thin polymer foil, in which light is coupled and carried by means of special coupling structures. In the process, the coupling structure is created at the surface of the foils, rather than on the edge of the foil. Another coupling structure can be used to decouple the light, wherein intensity in the foil (coupling efficiency) can be optimized.

The light is preferably coupled in a limited angular spectrum rather than a parallel light beam with only one irradiation angle. This achieves that the intensity distribution in the foil is homogenized after an inflow distance. If the initial beam was parallel, the individual reflexes of the light would appear bright on both surfaces, while the areas between the reflective areas would not be illuminated. In this exemplary embodiment, the foil sensor has an area after the coupling structure in which no detection takes place and wherein said area only serves the homogenization of the intensity distribution.

The detection with the foil sensor at hand can be performed irrespective of the location.

The cross-sectional area of the coupling structure can correspond to a prism.

Moreover, the coupling structure can be a different refracting (refractive) optical element, such as e.g. a structure with a trapezoid or rectangular shape.

In the cross-section, the coupling structure can also delimit a round shape, such as e.g. comprise a semi-circle. Moreover, the coupling structure can be a diffractive element.

One thickness of the foil can range between 10 μm and 1,000 μm.

The detected reactions can be DNA-DNA hybridizations, immunoreactions or other reactions which lead to the alteration of the fluorescence properties at one of the surfaces.

Instead of measuring the fluorescence properties of media bound to the surface, the absorption of the carried light and its change can be determined, by detecting the intensity at the output of the decoupling structure.

The fluorescence properties to be detected can also be properties found inside the foil rather than on the foil surface. In this case, the foil itself has sensory properties and absorbs materials from the surroundings.

Furthermore, the absorption of molecules at the foil surface can be replaced with the absorption of the light in the foil itself.

Where several embodiments have been discussed, those skilled in the art recognize that the words used in the description are words of description, and not words of limitation. Many variations and modifications will become apparent to those skilled in the art without departing from the scope and spirit of the invention, as set forth in the appended claims.

The invention claimed is:

1. A device for optical detection of substances in a liquid or gaseous medium, comprising:
   a substrate with fluorescent molecules immobilized thereto for detecting substances that are selectively bindable to said fluorescent molecules;
   said substrate comprising a polymeric foil element comprising an optically transparent plastic material having a thickness of from 10 to 1000 microns;
   said foil element having at least one light wave coupling structure capable of guiding coupled light waves, the light wave coupling structure including a prism; and
   said coupling structure being integrally formed with the foil element at a surface of the foil element, said coupling structure being located at an area of the foil element adapted to be brought into contact with the substances to be detected, wherein the coupling structure is a refractive optical element;

wherein the prism is provided for simultaneously with the formation of the film in a mold made for coining, rolling or injection molding, and the prism is provided for in one step with the making of the device.

2. A device for optical detection of substances in a liquid or gaseous medium, comprising:
   a substrate with fluorescent molecules immobilized thereto for detecting substances that are selectively bindable to said fluorescent molecules;
   said substrate comprising a polymeric foil element comprising an optically transparent plastic material having a thickness of 10 to 1000 microns;
   said foil element having at least one light wave coupling structure capable of guiding coupled light waves, the light wave coupling structure including a prism, the coupling structure being integrally formed with the foil element at a surface of the foil element, the coupling structure located at an area of the foil element adapted to be brought into contact with the substance to be detected, wherein the coupling structure is a refractive optical element; and
   a flow cell for the medium to be examined, said flow cell forming a measurement area with a surface of the foil element, wherein the coupling structure is in the measurement area;
   wherein the prism is provided for simultaneously with the formation of the film in a mold made for coining, rolling or injection molding, and the prism is provided for in one step with the making of the device.

3. The device according to claim 2, wherein the immobilized molecules are probes comprising biological or biochemical molecules selected from the group consisting of antibody molecules, DNA molecules, DNA single strands, RNA molecules, RNA single strands, and mixtures thereof.

4. The device according to claim 1, wherein the immobilized molecules form a readout field with a multiplicity of measurement points for spatially-resolved detection of the selectively bindable substances.

5. The device according to claim 4, wherein the foil element has an homogenizing area in a beam path downstream of the coupling structure and upstream of the readout field.

6. The device according to claim 4, further including a light wave homogenizing element in a beam path downstream of the coupling structure and upstream of the measurement points.

7. The device according to claim 2, wherein the coupling structure has a curvature.

8. The device according to claim 2, wherein the coupling structure is a diffractive optical element.

9. The device according to claim 1, wherein said foil element has a thickness of up to 130 µm.

10. The device according to claim 9, wherein the foil element is includes an outer area that frames an inner area, the outer area having a thickness greater than a thickness of the inner area.

11. The device according to claim 2, wherein the foil element is integrated into a polymer cartridge, said polymer cartridge having an injection port for the medium that is to be examined, reagent containers, fluid canals for transporting the medium and reagents, and devices for moving the medium and the reagents.

12. A device for optical detection of substances in a liquid or gaseous medium, comprising:
   a substrate with fluorescent molecules immobilized thereto for detecting substances that are selectively bindable to said fluorescent molecules;
   said substrate comprising a polymeric foil element comprising an optically transparent plastic material having a thickness of 10 to 1000 microns in which a coupling structure capable of guiding light waves is integrally formed at a surface of the foil element, the light wave coupling structure including a prism, the coupling structure being located at an area of the foil element adapted to be brought into contact with the substances to be detected, wherein the coupling structure is a refractive optical element; and
   said coupling structure comprising excitation optics for producing light waves for exciting a label used for optical detection, or for producing a color change at the foil element;
   wherein the prism is provided for simultaneously with the formation of the film in a mold made for coining, rolling or injection molding, and the prism is provided for in one step with the making of the device.

13. The device according to claim 12, further including a device for changing a relative position of excitation optics to the coupling structure, wherein a coupling angle can be selected to roughly correspond to a total reflection angle to provide a refractive index of the medium adjacent to the foil element.

14. The device according to claim 13, further including a decoupling structure in the foil element, wherein the decoupling structure is for decoupling coupled light waves and is formed at the surface of the foil element during formation step of the foil element.

15. The device according to claim 14, wherein the decoupling structure is a refractive optical element or a diffractive optical element.

16. The device according to claim 15, wherein a detector is in a beam path downstream of the decoupling structure, wherein the light waves decoupled from the decoupling structure can be detected by this detector for optimizing the beam position or for determining the scattered light of the coupled light waves.

17. The device according to claim 15, wherein a detector for detection of an intensity of the light waves is provided at the decoupling structure for determining absorption of the light waves guided in the foil element and the associated change of energy state of the light waves.

18. The device according to claim 3, further comprising focusing optics with which optical characteristics of substances or labels bound to the probes can be measured.

19. The device according to claim 1, wherein optically transparent plastic material comprises an organic polymer or copolymer.

20. The device according to claim 18, wherein the foil element comprises a hot stamped glass.

21. The device according to claim 1, wherein said molecules are immobilized at a surface of said substrate.

22. The device according to claim 1, wherein said molecules are immobilized in said substrate.

23. The device according to claim 6, wherein said light wave homogenizing element is a diffraction grating.

24. The device according to claim 2, wherein the refractive optical element is a prism or a grating or a structure with a trapezoidal or rectangular cross-section.

25. The device according to claim 10, wherein said outer area provides increased mechanical stability to the foil element.

26. The device according to claim 12, wherein said label is a fluorescent dye.

27. The device according to claim 12, wherein said foil element has a thickness of about 100 microns.

28. The device according to claim 18, wherein said optical characteristics comprise fluorescence or color.

29. The device according to claim 2, wherein said foil element has a thickness of up to 130 microns.

* * * * *